United States Patent
Han et al.

(10) Patent No.: US 10,151,676 B2
(45) Date of Patent: Dec. 11, 2018

(54) REFRIGERATOR WITH FERMENTED BEVERAGE RANCIDITY SENSOR AND CONTROL METHOD THEREOF

(71) Applicant: Samsung Electronics Co., Ltd., Suwon-si (KR)

(72) Inventors: Kyu Sun Han, Suwon-si (KR); Yoon Young Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 84 days.

(21) Appl. No.: 15/207,815

(22) Filed: Jul. 12, 2016

(65) Prior Publication Data
US 2017/0030631 A1 Feb. 2, 2017

(30) Foreign Application Priority Data
Jul. 30, 2015 (KR) .................. 10-2015-0108015

(51) Int. Cl.
| | | |
|---|---|---|
| F25D 29/00 | (2006.01) | |
| G01N 5/02 | (2006.01) | |
| G01N 33/14 | (2006.01) | |

(52) U.S. Cl.
CPC .............. *G01N 5/02* (2013.01); *F25D 29/00* (2013.01); *G01N 33/146* (2013.01); *F25D 2331/803* (2013.01); *F25D 2400/361* (2013.01)

(58) Field of Classification Search
CPC ........ G01N 5/02; G01N 33/146; F25D 29/00; F25D 31/007; F25D 2331/803; F25D 2400/361
See application file for complete search history.

(56) References Cited

U.S. PATENT DOCUMENTS

| | | | | |
|---|---|---|---|---|
| 5,802,863 A | * | 9/1998 | Cowans | F25D 31/007 165/295 |
| 8,747,775 B2 | * | 6/2014 | Sandvick | G08B 5/36 422/105 |
| 2010/0199709 A1 | * | 8/2010 | Holland | F25D 11/02 62/447 |
| 2014/0201182 A1 | * | 7/2014 | Amin | G01N 33/0031 707/706 |
| 2015/0000371 A1 | * | 1/2015 | Greene | G01N 33/146 73/19.1 |

FOREIGN PATENT DOCUMENTS

KR 10-0786255 12/2007

* cited by examiner

*Primary Examiner* — Jonathan Bradford
(74) *Attorney, Agent, or Firm* — Staas & Halsey LLP

(57) ABSTRACT

Disclosed herein are a refrigerator of sensing a degree of rancidity of fermented beverage to transmit state information of the fermented beverage to a remote user, and a method of controlling the refrigerator. The refrigerator may include a storage space configured to store fermented beverage, a cooling unit configured to cool inside air of the storage space; a rancidity sensor configured to sense a degree of rancidity of the fermented beverage, and a communication device configured to transmit state information of the fermented beverage created based on the degree of rancidity to a predetermined external device.

20 Claims, 18 Drawing Sheets

REFRIGERATOR WITH FERMENTED BEVERAGE RANCIDITY SENSOR AND CONTROL METHOD THEREOF

CROSS-REFERENCE TO RELATED APPLICATION

This application claims the benefit of Korean Patent Application No. 10-2015-0108015, filed on Jul. 30, 2015 in the Korean Intellectual Property Office, the disclosure of which is incorporated herein by reference.

BACKGROUND

1. Field

Embodiments of the present disclosure relate to a refrigerator capable of storing food including fermented beverage, and a method of controlling the refrigerator.

2. Description of the Related Art

In general, a refrigerator is a home appliance including a storage space for storing food and a cool air supply unit for supplying cool air to the storage space to keep the food fresh.

Lately, refrigerators for specific food are being introduced. Examples of the refrigerators for specific food include a fermentation refrigerator for storing fermented food in optimum state, and a wine refrigerator for storing wine in optimum state.

Particularly, since fermented beverage such as wine is rancidified from when the cap opens so that the fermented beverage is exposed to the air, studies into a refrigerator capable of preventing such rancidity are actively conducted.

SUMMARY

Therefore, it is an aspect of the present disclosure to provide a refrigerator of sensing a degree of rancidity of fermented beverage to transmit state information of the fermented beverage to a remote user, and a method of controlling the refrigerator.

Additional aspects of the disclosure will be set forth in part in the description which follows and, in part, will be obvious from the description, or may be learned by practice of the disclosure.

In accordance with one aspect of the present disclosure, a refrigerator includes a storage space configured to store fermented beverage; a cooling unit configured to cool inside air of the storage space; a rancidity sensor configured to sense a degree of rancidity of the fermented beverage; and a communication unit configured to transmit state information of the fermented beverage created based on the degree of rancidity to a predetermined external device.

The rancidity sensor may sense the degree of rancidity of the fermented beverage using the fermented beverage in a gaseous state.

The rancidity sensor may sense the degree of rancidity of the fermented beverage, based on mass of the fermented beverage in the gaseous state absorbed on a plurality of different polymers.

The refrigerator may further include a controller configured to create the state information of the fermented beverage based on the degree of rancidity of the fermented beverage.

The controller may create the state information of the fermented beverage, including at least one of a rancidity degree percentage, an expected date of rancidity, and a recommended drinkable period of the fermented beverage, based on the degree of rancidity of the fermented beverage.

If a present date falls within a predetermined time period before the expected date of rancidity or if the present date passes the recommended drinkable period, the controller may control the communication unit to transmit a rancidity warning message to the external device.

The controller may control the communication unit to transmit a rancidity warning message including rancidity delay temperature for inside air of the storage space to the external device.

The storage space may include a first storage space whose inside air is cooled to first temperature by the cooling unit; and a second storage space whose inside air is cooled to second temperature by the cooling unit, wherein the second temperature is lower than the first temperature, wherein the controller controls the communication unit to transmit a rancidity warning message including a position movement guide message for guiding a user to move the fermented beverage to the second storage space, to the external device.

If a present date falls within a predetermined time period before the expected date of rancidity or if the present date passes the recommended drinkable period, the controller may control the cooling unit to cool inside air of the storage space to predetermined rancidity delay temperature.

If the controller receives a control command for cooling the inside air of the storage space to the rancidity delay temperature from the external device when the present date falls within the predetermined time period before the expected date of rancidity or when the present date passes the recommended drinkable period, the controller may control the cooling unit according to the control command.

If the controller receives a control command for deciding a target date of rancidity from the external device when the present date falls within the predetermined time period before the expected date of rancidity or when the present date passes the recommended drinkable period, the controller may control the cooling unit to cool the inside air of the storage space to rancidity delay temperature decided according to the target date of rancidity.

The refrigerator may further include a cap opener configured to draw a cap inserted into an opening of a container in which the fermented beverage is contained, wherein the rancidity sensor is disposed in the inside of the cap opener.

The cap opener may include a guide part configured to guide the cap inserted into the opening of the container to the inside of the cap opener; and a uncapping part configured to draw the cap entered the inside of the cap opener along the guide part out of the opening, wherein the rancidity sensor is disposed to face the opening of the container when the cap is drawn out of the opening.

In accordance with another aspect of the present disclosure, a method of controlling a refrigerator, the refrigerator including a storage space to store fermented beverage, the method includes sensing a degree of rancidity of the fermented beverage; creating state information of the fermented beverage based on the degree of rancidity; and transmitting the state information of the fermented beverage to a predetermined external device.

The sensing of the degree of rancidity of the fermented beverage may include sensing the degree of rancidity of the fermented beverage using the fermented beverage in a gaseous state.

The sensing of the degree of rancidity of the fermented beverage may include sensing the degree of rancidity of the fermented beverage based on mass of the fermented beverage in the gaseous state absorbed on a plurality of different polymers.

The creating of the state information of the fermented beverage may include creating the state information of the fermented beverage, including at least one of a rancidity degree percentage, an expected date of rancidity, and a recommended drinkable period of the fermented beverage, based on the degree of rancidity of the fermented beverage.

The method may include transmitting a rancidity warning message to the external device, if a present date falls within a predetermined time period before the expected date of rancidity or if the present date passes the recommended drinkable period.

The transmitting of the rancidity warning message to the external device comprises transmitting a rancidity warning message including rancidity delay temperature for inside air of the storage space to the external device.

The method may further include cooling inside air of the storage space to predetermined rancidity delay temperature, if a present date approaches the expected date of rancidity within a predetermined time period or if the present date passes the recommended drinkable period.

The cooling of the inside air of the storage space to the predetermined rancidity delay temperature may include receiving a control command for cooling the inside air of the storage space to the rancidity delay temperature from the external device, if a present date falls within a predetermined time period before the expected date of rancidity or if the present date passes the recommended drinkable period; and cooling the inside air of the storage space according to the control command.

The cooling of the inside air of the storage space to the predetermined rancidity delay temperature may include receiving a control command for deciding a target date of rancidity from the external device, if the present date falls within the predetermined time period before the expected date of rancidity or if the present date passes the recommended drinkable period; and cooling the inside air of the storage space to rancidity delay temperature decided according to the target date of rancidity.

The method may further include, if a present date falls within a predetermined time period before the expected date of rancidity or if the present date passes the recommended drinkable period, transmitting, to the external device, a position movement guide message for guiding a user to move the fermented beverage stored in a first storage space whose inside air is maintained at first temperature to a second storage space whose inside air is maintained at second temperature that is lower than the first temperature, wherein the first storage space and the second storage space are provided in the storage space.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 9 is a flowchart illustrating a method of transmitting state information of wine.

FIG. 10 is a flowchart illustrating a method of transmitting a rancidity warning message, according to an embodiment of the present disclosure.

FIG. 11 is a flowchart illustrating a method of transmitting a rancidity warning message, according to another embodiment of the present disclosure.

FIG. 12 is a flowchart illustrating a method of cooling the inside air of a storage space to rancidity delay temperature.

DETAILED DESCRIPTION

Figure 1:
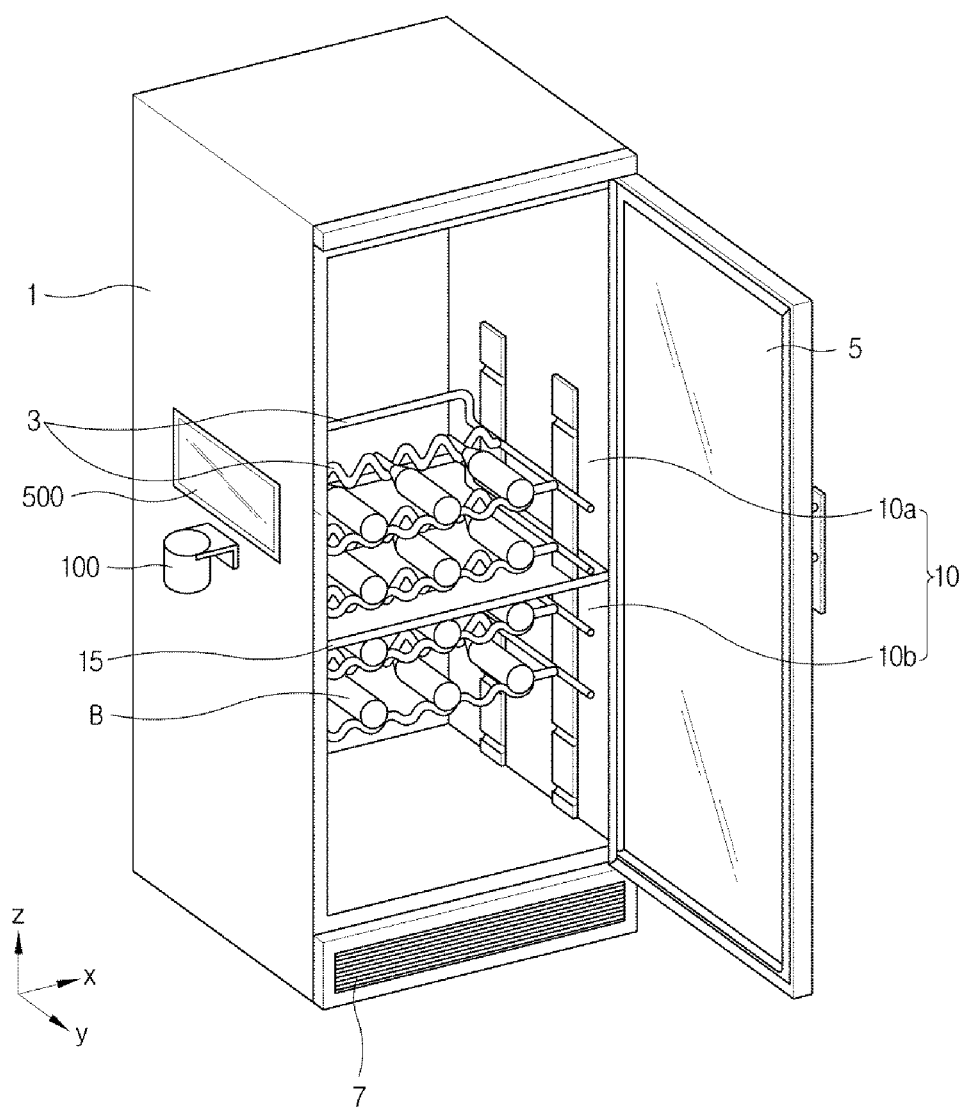
FIG. 1 shows an outer appearance of a refrigerator according to an embodiment of the present disclosure.

Hereinafter, an embodiment of the present disclosure will be described in detail with reference to the accompanying drawings. In the drawings, like reference numerals or symbols represent members or components performing the substantially same functions.

Hereinafter, for convenience of description, a refrigerator for storing wine as an example of fermented beverage will be described, however, the technical features of the present disclosure can be applied to any other kind of refrigerator.

Figure 2:
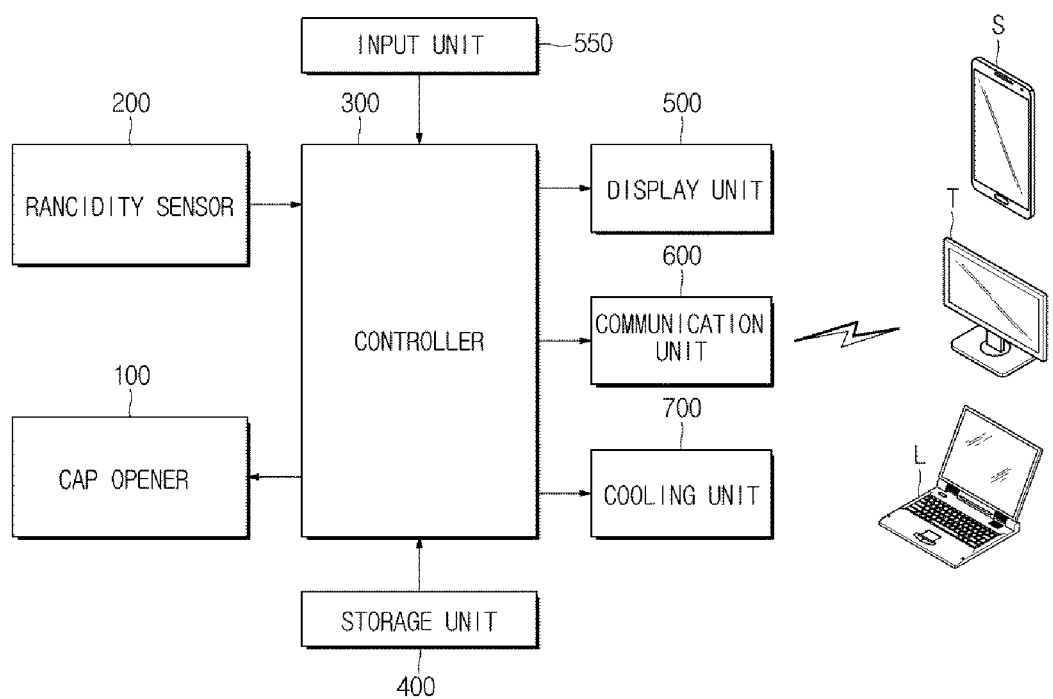
FIG. 2 is a control block diagram of a refrigerator according to an embodiment of the present disclosure.
Figure 3:
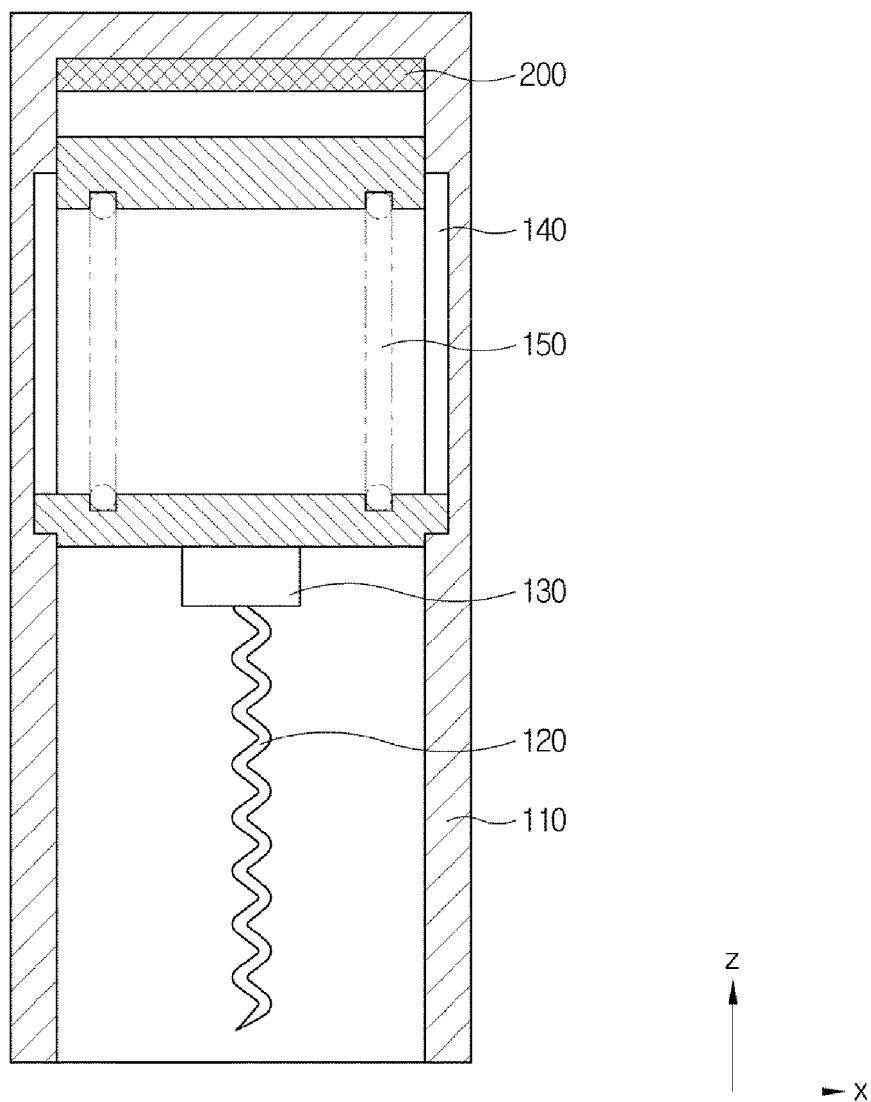
FIG. 3 is a cross-sectional view of a cap opener according to an embodiment of the present disclosure.
Figure 4:
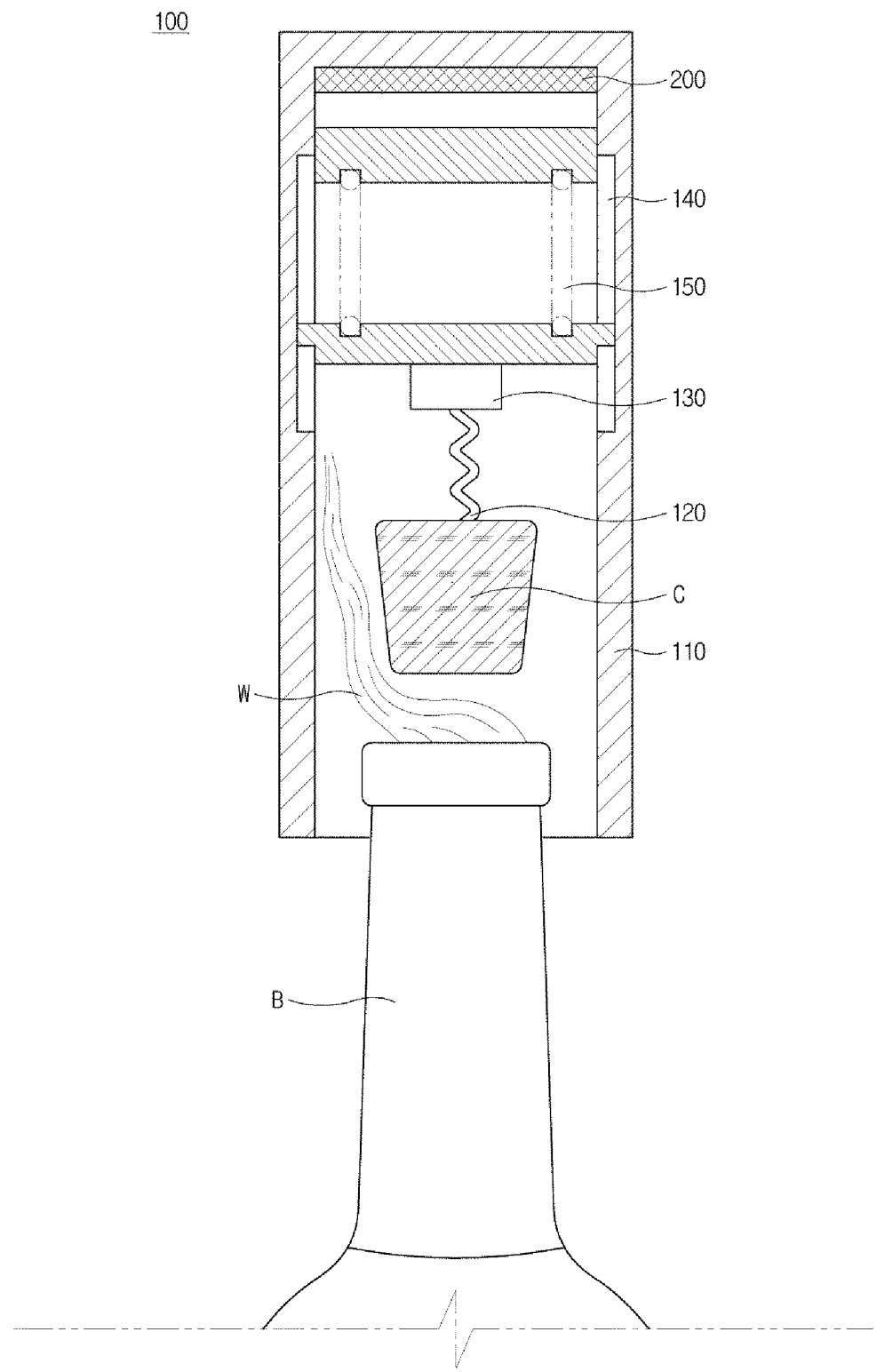
FIG. 4 is a view for describing a method in which a rancidity sensor according to an embodiment of the present disclosure senses a degree of rancidity.

FIG. 1 shows an outer appearance of a refrigerator according to an embodiment of the present disclosure, FIG. 2 is a control block diagram of a refrigerator according to an embodiment of the present disclosure, FIG. 3 is a cross-sectional view of a cap opener according to an embodiment of the present disclosure, and FIG. 4 is a view for describing a method in which a rancidity sensor according to an embodiment of the present disclosure senses a degree of rancidity.

Referring to FIGS. 1 and 2, a refrigerator according to an embodiment of the present disclosure may include a main body 1 forming an outer appearance of the refrigerator and including a storage space 10 for storing wine; a wine rack 3 installed in the storage space 10 and configured to store a plurality of wine bottles B; a cooling unit 700 configured to cool the inside air of the storage space 10; a door 5 configured to open or close the storage space 10; a display unit 500 configured to visually display various kinds of information; an input unit 550 configured to receive a control command from a user; a controller 300 configured to control the refrigerator according to a received control command; and a storage unit in which information related to the control of the refrigerator is stored in advance.

In the main body 1, a machine room 7 may be provided, and the cooling unit 700 for supplying cool air to the storage space 10 may be installed. The cooling unit 700 may maintain the temperature of the storage space 10 within a constant temperature range using the evaporation of refrigerants. The cooling unit 700 according to an embodiment of the present disclosure may supply cool air to the storage space 10 using a phenomenon in which liquid refrigerants absorb thermal energy of ambient air when decompressed and converted into a gaseous state. Also, the cooling unit 700 according to another embodiment of the present disclosure may cool the inside air of the storage space 10 using the Peltier effect. Also, the cooling unit 700 may maintain the temperature of the storage space 10 using the Magneto-Caloric effect.

The storage space 10 of the main body 1 may be partitioned into a first storage space 10a and a second storage space 10b by an intermediate partition wall 15, wherein the first storage space 10a is the upper part of the storage space 10, and the second storage space 10b is the lower part of the storage space 10. The first storage space 10a and the second storage space 10b may be cooled to different temperatures by the cooling unit 700. As such, by partitioning the storage space 10 into the first storage space 10a and the second storage space 10b, and maintaining the first and second storage spaces 10a and 10b at different temperatures, the refrigerator can store various kinds of wine.

For example, red wine needs to be stored preferably within a temperature range of about 14° C. to 18° C., and white wine needs to be stored preferably within a temperature range of about 8° C. to 13° C., in order to keep the taste and flavor of the wine. Accordingly, by maintaining the inside temperature of the first storage space 10a within a temperature range of 14° C. to 18° C., and the inside temperature of the second storage space 10b within a temperature range of 8° C. to 13° C., the refrigerator can provide an optimum environment for storing red wine and white wine.

The door 5 may be rotatably connected to the front part of the main body 1. A user may rotate the door 5 to open or close the storage space 10 of the refrigerator. In FIG. 1, a case in which the refrigerator includes a single door 5 is shown, however, the refrigerator may include a plurality of doors to open or close the first storage space 10a and the second storage space 10b, respectively.

In the storage space 10, a plurality of wine racks 3 may be installed to store a plurality of wine bottles B. The wine racks 3 may be inclined downward towards the door 5. Wine contained in the wine bottles put on the inclined wine racks 3 may wet corks C so that the refrigerator can prevent the corks C from drying and contracting.

The slope of the wine rack 3 according to an embodiment may be adjusted automatically or manually. For example, if the storage space 10 is closed by the door 5, the wine rack 3 may be inclined downward towards the door 5, and if the door 5 rotates to open the storage space 10, the wine rack 3 may be inclined upward towards the door 5. As a result, when the user rotates the door 5 to open the storage space 10, the wine bottles B can be prevented from falling out of the refrigerator.

The display unit 500 may be provided on the outer surface of the refrigerator to provide the user with various kinds of information. For example, the display unit 500 may display information (for example, information about goods stored in the storage space 10, the temperature of the storage space 10, etc.) related to the refrigerator, or information (for example, weather, date, time, etc.) unrelated to the refrigerator. Also, the display unit 500 may display a user interface for receiving control commands from a user.

In order to display the information, the display unit 500 may be implemented with a Liquid Crystal Display (LCD) panel, a Light Emitting Diode (LED) panel, or an Organic Light Emitting Diode (OLED) panel.

The input unit 550 may receive a control command from the user. For example, the input unit 550 may receive a command for powering on/off the refrigerator, a command for setting the inside temperature of the storage space 10, etc.

In FIG. 1, a case in which the input unit 550 is implemented as a touch screen together with the display unit 500 is shown. In this case, the user may touch a screen displayed on the display unit 500 to thereby input a control command.

Unlike this, the input unit 550 may be provided on the outer surface of the refrigerator, separately from the display unit 500. For example, the input unit 550 may be implemented in the form of a pressure button, a capacitive button, a keyboard, a joystick, a track ball, or a jog shuttle, on the outer surface of the refrigerator.

The controller 300 may control the refrigerator according to a control command input through the input unit 550. For example, if a command for powering on/off the refrigerator is input through the input unit 550, the controller 300 may power on/off the refrigerator. Also, if a command for setting the inside temperature of the storage space 10 is input through the input unit 550, the controller 300 may cool the inside air of the storage space 10 according to temperature input by the user.

The controller 300 may use information stored in advance in the storage unit to control the refrigerator. In the storage unit, various kinds of setting values that are used to control the refrigerator may be stored to be provided to the controller 300 as necessary. For this, the storage unit may be implemented as at least one of a flash memory type, a hard disk type, a multimedia card micro type, a card type memory (for example, Secure Digital (SD) memory or Extreme Digital (EX) memory), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disk, and an optical disk.

The controller 300 may be hardwarily implemented in the form of a processor, or implemented as software that is executed on a processor.

Meanwhile, fermented beverage such as wine is rancidified from when the cap opens so that the fermented beverage is exposed to the air. Rancidity of beverage means a phenomenon in which beverage is hydrolyzed or oxidized by reacting with oxygen, light, heat, germs, enzymes, etc. in the air to produce various kinds of oxides. Rancidified fermented beverage may smell bad while changing color and taste. Accordingly, there needs to be provided a refrigerator capable of informing a user of state information of fermented beverage related to rancidity to directly or indirectly control a storage environment for the fermented beverage according to the state information of the fermented beverage.

In order to provide a user with state information created based on a degree of rancidity of fermented beverage, the refrigerator according to an embodiment of the present disclosure may further include: a cap opener 100 configured to draw a cap from a wine bottle B; a rancidity sensor 200 configured to sense a degree of rancidity of wine; and a communication unit 600 configured to transmit state information of wine created based on a degree of rancidity to a predetermined external device.

As shown in FIG. 1, the cap opener 100 may be disposed on the outer surface of the main body 1 in order to draw a cap from a wine bottle B. However, the cap opener 100 may be disposed in an inside space formed by the main body 1, or may be separated from the main body 1.

Referring to FIGS. 3 and 4, the cap opener 100 may include a guide part 110 configured to guide a cap inserted in the opening of a wine bottle B to the inside of the cap opener 100; a uncapping part 120 configured to draw the cap entered the inside of the cap opener 100 along the guide part 110 out of the opening of the wine bottle B; a motor 130 configured to supply a turning force to the uncapping part 120; a conveying part 140 configured to move the uncapping part 120 in a up-and-down direction; and a spring 150 configured to restore the position of the uncapping part 120 to which external pressure is applied.

The guide part 110 may be shaped to surround the outer surface of the wine bottle B so as to help the wine bottle B enter a position at which the uncapping part 120 can be inserted into the cap.

The uncapping part 120 may be shaped to be inserted into the cap of the wine bottle B. If the cap of the wine bottle B is a cork C, the uncapping part 120 may be implemented as a wire type screw, or in the shape of a shaft with a spiral protrusion.

The motor 130 may transfer a turning force to the uncapping part 120 so that the uncapping part 120 can be inserted into the cap. If the cap of the wine bottle B is a cork C, the motor 130 may rotate the uncapping part 120 to help the uncapping part 120 be easily inserted into the cork C.

The conveying part 140 may move the uncapping part 120 in the up-and-down direction. More specifically, when the uncapping part 120 is inserted into the cap, the conveying part 140 may move the rotating uncapping part 120 in the down direction (that is, in a negative z-axis direction). Also, after the uncapping part 120 is sufficiently inserted into the cap, the conveying part 140 may move the uncapping part 120 rotating no longer in the up direction (that is, in a positive z-axis direction). As a result, the cap may be drawn out of the wine bottle B.

The spring 150 may provide a restoring force to the uncapping part 120 so as to draw the cap stably. More specifically, if the conveying part 140 moves the uncapping part 120 in the down direction, a normal force by the cap of the wine bottle B may be applied to the uncapping part 120. At this time, the spring 150 may transfer a restoring force to the uncapping part 120 in a direction that is opposite to the normal force, so as to help the uncapping part 120 be stably inserted into the cap.

Unlike this, the cap opener 100 may not include at least one of the motor 130 and the conveying part 140. If the cap opener 100 does not include the motor 130, the user may rotate the wine bottle B so as for the uncapping part 120 to be inserted into the cap. Also, if the cap opener 100 does not include the conveying part 140, the user may pull the wine bottle B in the down direction when the uncapping part 120 is sufficiently inserted into the cap, thereby drawing the cap from the wine bottle B.

The rancidity sensor 200 may sense a degree of rancidity of wine. More specifically, the rancidity sensor 200 may use wine W in a gaseous state in the inside of the wine bottle B to sense a degree of rancidity of the wine. In order to sense a degree of rancidity of wine, the rancidity sensor 200 may be provided in the inside of the cap opener 100.

FIG. 4 shows a case in which a cap is drawn out of a wine bottle B by the cap opener 100. In the inside of the wine bottle B, wine in a liquid state and wine W in a gaseous state may coexist. If the wine bottle B opens, the wine W in the gaseous state may be discharged to the outside through the opening of the wine bottle B. Since the wine bottle B is positioned in the inside of the cap opener 100, the wine W in the gaseous state may also be diffused in the inside of the cap opener 100. Accordingly, the rancidity sensor 200 may also be disposed in the inside of the cap opener 100 to sense a degree of rancidity from the diffused wine W in the gaseous state.

In FIG. 4, a case in which the rancidity sensor 200 is located at the upper portion of the cap opener 100 is shown. However, the location of the rancidity sensor 200 is not limited as long as it is located in the inside of the cap opener 100.

The rancidity sensor 200 may compare a result of reaction with the wine W in the gaseous state to predetermined reference data to sense a degree of rancidity of the wine. Since rancidified wine produces specific oxides, the rancidity sensor 200 may measure the density of oxides produced as the results of rancidity to sense a degree of rancidity.

The rancidity sensor 200 may sense a degree of rancidity using one of various methods well-known in the art. For example, the rancidity sensor 200 may decide a degree of rancidity of wine based on reactivity with a specific material.

More specifically, the rancidity sensor 200 may use a polymer. Polymers which are materials capable of absorbing oxides in a gaseous state produced as the results of rancidity may show different absorption characteristics according to their kinds.

The rancidity sensor 200 may expose the polymer to the wine W in the gaseous state. The polymer may increase its mass by absorbing gas containing oxides produced as the results of rancidity. The rancidity sensor 200 may compare a change in mass of the polymer to predetermined reference data to thus sense a degree of rancidity.

The reference data may be decided as the results of reaction of wine with the polymer when predetermined conditions, such as the time of exposure to the air, the degree of exposure to the air, storage temperature, etc., change. The reference data may include a value of reaction of wine with the polymer at the time when rancidity occurs.

The rancidity sensor 200 may search for the sensed change in mass of the polymer in the reference data, and compare the sensed change in mass of the polymer to the value of reaction at the time when rancidity occurs, thereby sensing a degree of rancidity.

Also, the rancidity sensor 200 may use a plurality of different polymers. Since polymers show different absorption characteristics according to their kinds, the rancidity sensor 200 may use a plurality of polymers capable of respectively absorbing a plurality of oxides produced as the results of rancidity to sense a degree of rancidity of wine. Thereby, the rancidity sensor 200 may increase the accuracy of a sensed degree of rancidity.

The controller 300 may create state information of the wine based on the degree of rancidity sensed by the rancidity sensor 200. Herein, the state information may be a value obtained by processing the degree of rancidity so that the user can easily recognize the degree of rancidity. The state information may include a rancidity degree percentage, a recommended drinkable period, and an expected date of rancidity, etc.

The communication unit 600 may transmit the state information of the wine to a predetermined external device according to the control of the controller 300. The predetermined external device may include all kinds of electronic devices that can transmit/receive data to/from the refrigerator according to a communication method adopted by the communication unit 600. Particularly, the predetermined external device may provide the user with the state information of the wine received from the communication unit 600, visually, acoustically, or tactually. In FIG. 2, a smart phone S, a television T, and a laptop computer L are shown as external devices communicating with the communication unit 600, however, the communication device 600 can communicate with any other external devices. External devices to which the communication unit 600 transmits state information of wine may be decided according to the user's setting or when the refrigerator is manufactured.

The communication unit 600 may communicate with the external device via a base station through a communication method, such as 3Generation (3G) communication and 4Generation (4G) communication. Also, the communication unit 600 may communicate with the external device within a predetermined range through a communication method, such as Wireless LAN (WLAN), Wireless-Fidelity (Wi-Fi), Bluetooth, Zigbee, Wi-Fi Direct (WFD), Ultra WideBand (UWB), Infrared Data Association (IrDA), Bluetooth Low Energy (BLE), and Near Field Communication (NFC).

Hereinafter, a method of displaying state information of wine in the external device according to the control of the controller 300 will be described in detail.

FIGS. 5A to 5D are views for describing methods of displaying state information of wine, according to various embodiments of the present disclosure. In FIGS. 5A to 5D, screens of a smart phone S displaying state information of wine are shown.

As described above, the controller 300 may create a rancidity degree percentage as state information of wine, based on a sensed degree of rancidity. The rancidity degree percentage may be a value obtained by converting a ratio of an actually sensed change in mass of the polymer with respect to a change in mass of the polymer at the time when rancidity occurs in the reference data into a percentage.

Figure 5A:
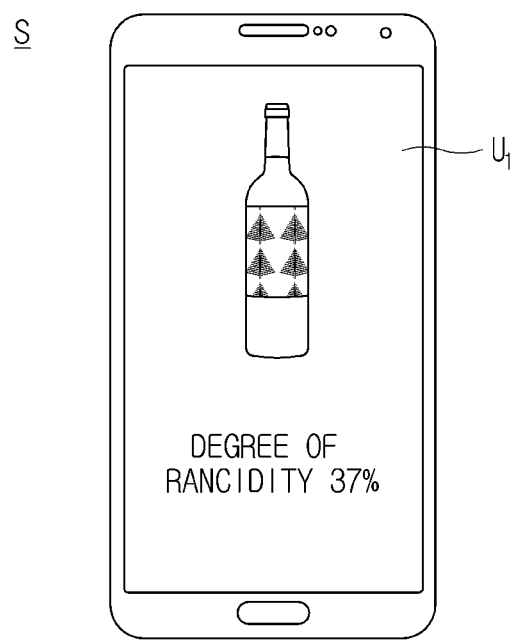
FIGS. 5A to 5D are views for describing methods of displaying state information of wine, according to various embodiments of the present disclosure.
Figure 5B:
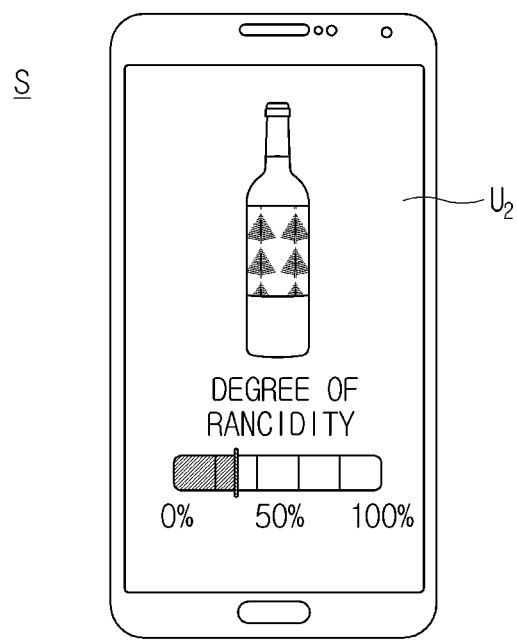

FIG. 5A shows a screen U1 that represents a rancidity degree percentage as an Arabic numeral, and FIG. 5B shows a screen U2 that represents a rancidity degree percentage in a bar type. Since the degree of rancidity acquired by the rancidity sensor 200 through comparison with the reference data is a relative value, the degree of rancidity may be converted into a percentage which is an absolute numerical value so as to provide the user with more definite information about a degree of progress of rancidity.

Unlike this, the controller 300 may create a recommended drinkable period as state information of wine, based on a sensed degree of rancidity. Herein, the recommended drinkable period may be a recommended drinkable period of wine having the currently sensed degree of rancidity. A degree of rancidity and a recommended drinkable period corresponding to the degree of rancidity may have been stored in the form of a table in advance in the storage unit. Alternatively, the controller 300 may calculate a recommended drinkable period based on a degree of rancidity. When calculating the recommended drinkable period, the controller 300 may refer to the above-described reference data.

Figure 5C:
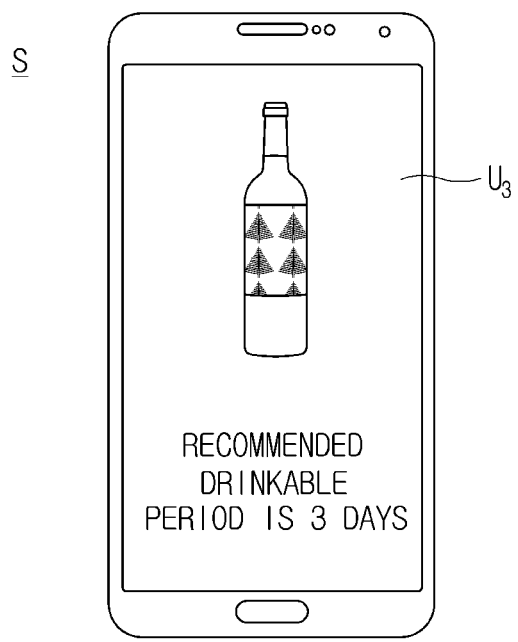

FIG. 5C shows a screen U3 displaying a recommended drinkable period. A user may visually check the recommended drinkable period displayed on the screen U3 to be able to recognize a period for which he/she can drink wine in an optimum state.

Also, the controller 300 may calculate an expected date of rancidity as state information of wine, based on a sensed degree of rancidity. Herein, the expected date of rancidity may be a date at which wine having a currently sensed degree of rancidity is expected to be rancidified. A degree of rancidity and an expected date of rancidity corresponding to the degree of rancidity may have been stored in the form of a table in advance in the storage unit. Alternatively, the controller 300 may calculate an expected date of rancidity based on a degree of rancidity. When calculating the expected date of rancidity, the controller 300 may refer to the above-described reference data.

Figure 5D:
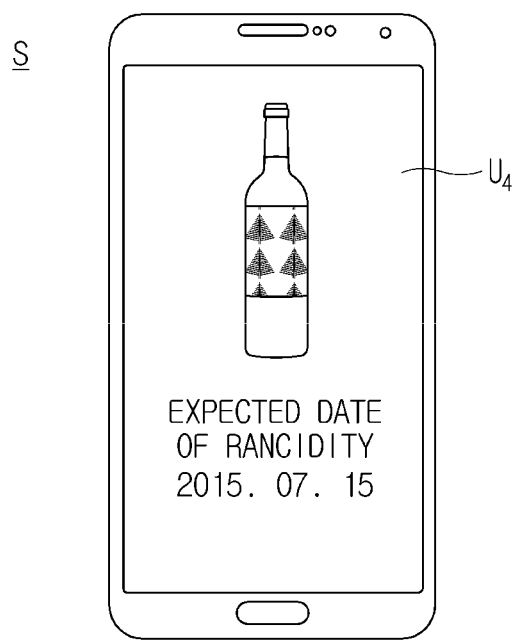

FIG. 5D shows a screen U4 displaying an expected date of rancidity. A user may visually check the expected date of rancidity displayed on the screen U4 to be able to drink wine before the expected date of rancidity.

Also, if a present date falls within a danger-of-rancidity time period, the controller 300 may control the communication unit 600 to transmit a rancidity warning message to the external device. Herein, the danger-of-rancidity time period may be a period for which a user needs to be warned that rancidity is imminent. For example, the danger-of-rancidity time period may be set to a predetermined time period before an expected date of rancidity or a predetermined time period after a recommended drinkable period.

In order to transmit the rancidity warning message to the external device, the controller 300 may determine whether the corresponding wine has been stored in the storage space 10. If the user has input information that the corresponding wine has been stored in the storage space 10, the controller 300 may recognize the user's input to control the communication unit 600 to transmit a rancidity warning message for the corresponding wine to the external device.

Figure 6A:
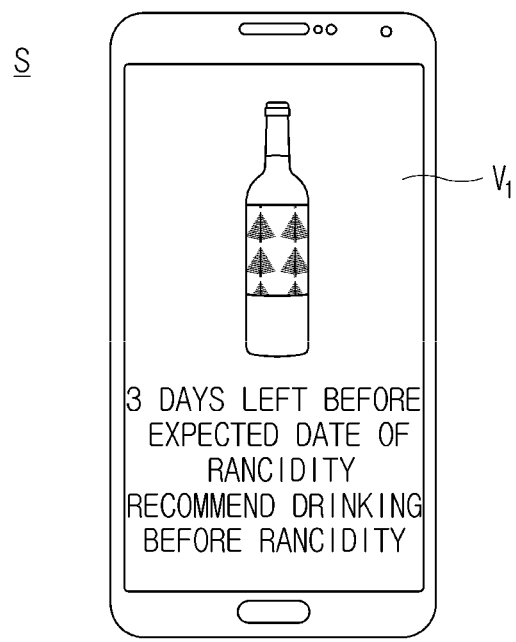
FIGS. 6A, 6B, and 6C are views for describing methods of displaying a rancidity warning message, according to various embodiments of the present disclosure.
Figure 6B:
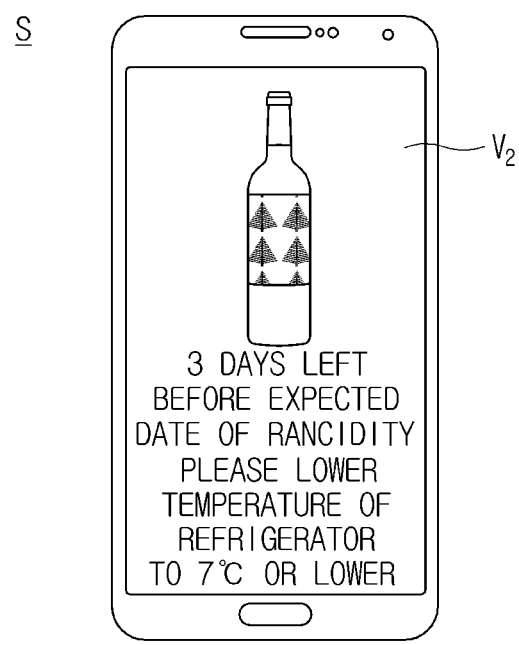
Figure 6C:
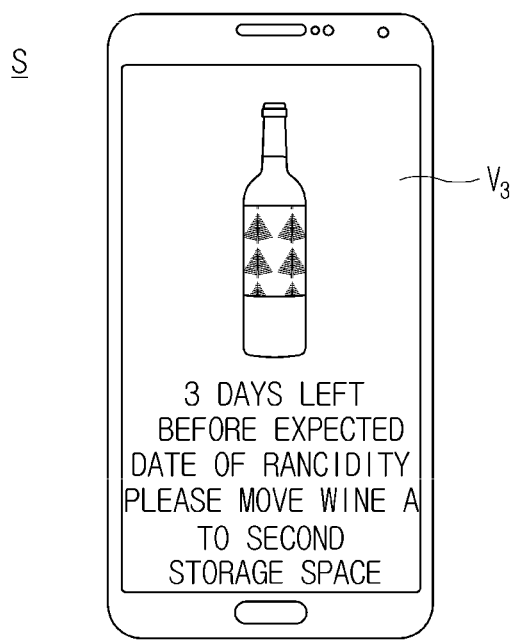

FIGS. 6A, 6B, and 6C are views for describing methods of displaying a rancidity warning message, according to various embodiments of the present disclosure. In FIGS. 6A, 6B, and 6C, screens of a smart phone S displaying rancidity warning messages are shown.

As described above, if a present date falls within a danger-of-rancidity time period, the controller 300 may create a rancidity warning message. For example, the controller 300 may create a rancidity warning message when a present date falls within a predetermined time period before an expected date of rancidity.

If an external device receives the rancidity warning message from the controller 300, the external device may display the rancidity warning message to warn a user that rancidity of the corresponding wine is imminent. In FIG. 6A, the smart phone S displays a screen V1 including a rancidity warning message warning that an expected date of rancidity is imminent.

In this way, the refrigerator may inform a remote user that an expected date of rancidity is imminent, so that the user can drink the corresponding wine before the wine is rancidified.

Also, the rancidity warning message may include rancidity delay temperature. Herein, the rancidity delay temperature may be inside temperature of the storage space 10 for delaying the expected date of rancidity of the corresponding wine. The controller 300 may decide the rancidity delay temperature based on state information of the wine.

FIG. 6B shows a screen V2 displaying a rancidity warning message including rancidity delay temperature. In FIG. 6B, the controller 300 may decide rancidity delay temperature as 7° C. based on information that three days left before an expected date of rancidity, and control the communication unit 600 so that a rancidity warning message including the rancidity delay temperature can be displayed through an external device.

In this way, the refrigerator may guide a remote user to lower inside temperature of the storage space 10 to delay rancidity of the wine, when the expected date of rancidity is imminent. Accordingly, the user can adjust the inside temperature of the storage space 10 to the rancidity delay temperature to thus delay rancidity of the wine.

Also, the rancidity warning message may include a position movement guide message for guiding the user to move the wine to another storage space in which rancidity can be delayed. If there is another storage space that is maintained at lower temperature than the storage space 10 in which the corresponding wine is stored, the controller 300 may control the communication unit 600 to guide the user to move the corresponding wine to the other storage space maintained at the lower temperature, through an external device.

In order to transmit the position movement guide message to the external device, the controller 300 may determine the storage space 10 in which the corresponding wine is stored. If the user has input information about the storage space 10 in which the corresponding wine is stored, the controller 300 may recognize the user's input to control the communication unit 600 to transmit a position movement guide message for guiding the user to move the wine to another storage space which is maintained at lower temperature than the storage space 10 in which the corresponding wine is stored, to the external device.

FIG. 6C shows a screen V3 displaying a rancidity warning message including a position movement guide message. In FIG. 6C, the controller 300 may determine that the corresponding wine is stored in the first storage space 10a based on information that three days left before an expected date of rancidity, and control the communication unit 600 to transmit a rancidity waning message including a position movement guide message for guiding the user to move the corresponding wine to the second storage space 10b that is maintained at lower temperature than the first storage space 10a, to an external device, so that the rancidity waning message can be displayed through the external device.

In this way, the refrigerator may guide a remote user to move the wine to the storage space maintained at the lower temperature, when the expected date of rancidity is imminent. Accordingly, the user can move the wine to the storage space maintained at the lower temperature to thus delay rancidity of the wine.

Also, if a present date falls within a danger-of-rancidity time period, the controller 300 may control the cooling unit 700 to cool inside air of the storage space 10 in which the wine is stored to rancidity delay temperature. More specifically, if a present date falls within a predetermined time period before an expected date of rancidity or passes a recommended drinkable period, the controller 700 may control the cooling unit 700 to automatically adjust inside temperature of the storage space 10 in which the wine is stored to the rancidity delay temperature.

Unlike this, if the controller 300 receives a first control command for cooling inside air to the rancidity delay temperature from the external device, the controller 300 may control the cooling unit 700 according to the first control command. For example, when a present date falls within the danger-of-rancidity time period, the controller 300 may control the communication unit 600 so that a first User Interface (UI) P for asking whether to cool inside air to the rancidity delay temperature is displayed on the external device.

Figure 7:
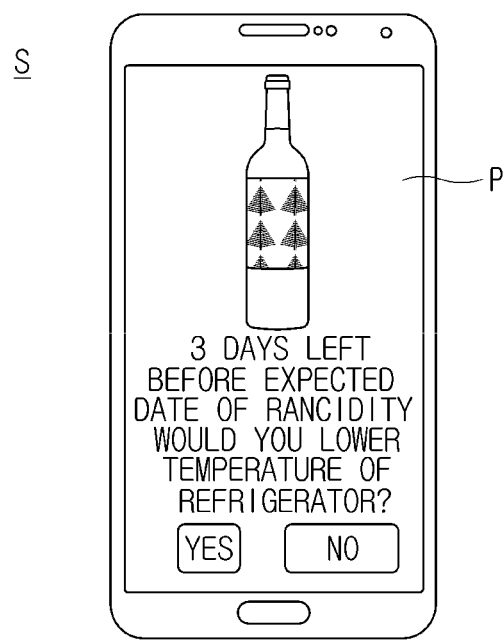
FIG. 7 is a view for describing a method of displaying a first UI P, according to an embodiment of the present disclosure.

FIG. 7 is a view for describing a method of displaying a first UI P, according to an embodiment of the present disclosure. In FIG. 7, a case in which the first UI P is displayed on a screen of a smart phone S is shown.

If an expected date of rancidity approaches to be within a predetermined time period, the controller 300 may control the communication unit 600 so that the first UI P is displayed on the smart phone S. As a result, the smart phone S may display the first UI P for asking whether to cool inside air to the rancidity delay temperature, as shown in FIG. 7. The user may recognize that three days left before an expected date of rancidity, and input a first control command for cooling the inside air of the storage space 10 to the rancidity delay temperature. If the communication unit 600 receives the first control command from the smart phone S, the controller 300 may control the cooling unit 700 according to the first control command to adjust the storage space 10 to the rancidity delay temperature.

Unlike this, if the controller 300 receives a second control command for deciding a target date of rancidity from an external device, the controller 300 may control the cooling unit 700 to cool the inside air of the storage space 10 to rancidity delay temperature decided according to the target date of rancidity. For this, if a present date falls within the danger-of-rancidity time period, the controller 300 may control the communication unit 600 so that a second UI Q1 for asking whether to set a target date of rancidity and a third UI Q2 for receiving an input of deciding a target date of rancidity are displayed on the external device.

Figure 8A:
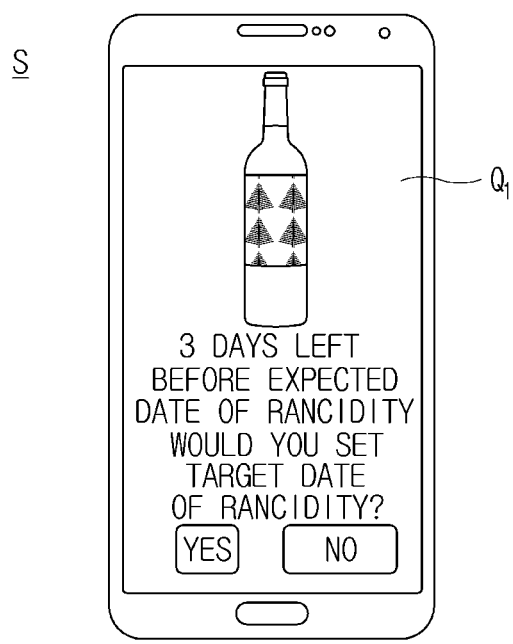
FIGS. 8A and 8B are views for describing a method of displaying a second UI and a third UI, according to an embodiment of the present disclosure.
Figure 8B:
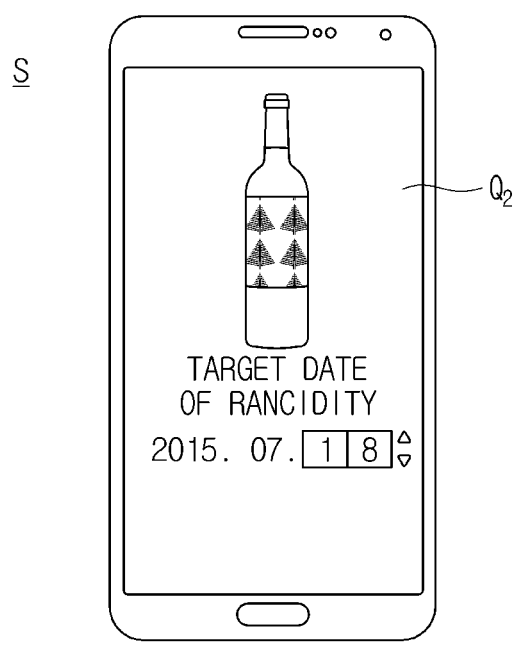

FIGS. 8A and 8B are views for describing a method of displaying a second UI and a third UI, according to an embodiment of the present disclosure. In FIGS. 8A and 8B, cases in which a second UI Q1 and a third UI Q2 are displayed on screens of a smart phone S are shown.

If an expected date of rancidity approaches to be within a predetermined time period, the controller 300 may control the communication unit 600 so that the smart phone S displays the second UI Q1. As a result, the smart phone S may display the second UI Q1 for asking whether to set a target date of rancidity, as shown in FIG. 8A. Then, a user may recognize that three days left before the expected date of rancidity, and select to decide a target date of rancidity.

In response to the user's selection, the smart phone S may display the third UI Q2 for receiving an input of deciding a target date of rancidity. Referring to FIG. 8B, the user may input a second control command for deciding a target date of rancidity through the third UI Q2. If the communication unit 600 receives a second control command for deciding a target date of rancidity from the smart phone S, the controller 300 may decide rancidity delay temperature according to the target date of rancidity. Then, the controller 300 may control the cooling unit 700 according to the decided rancidity delay temperature to adjust the storage space 10 to the rancidity delay temperature.

The above-described embodiments relate to a case in which the refrigerator is applied to wine, however, the refrigerator can be applied to fermented beverage which is a superordinate concept to wine. Also, the wine bottle B may be replaced with a container which is a superordinate concept to a wine bottle, and the smart phone S may be replaced with an external device.

Figure 9:
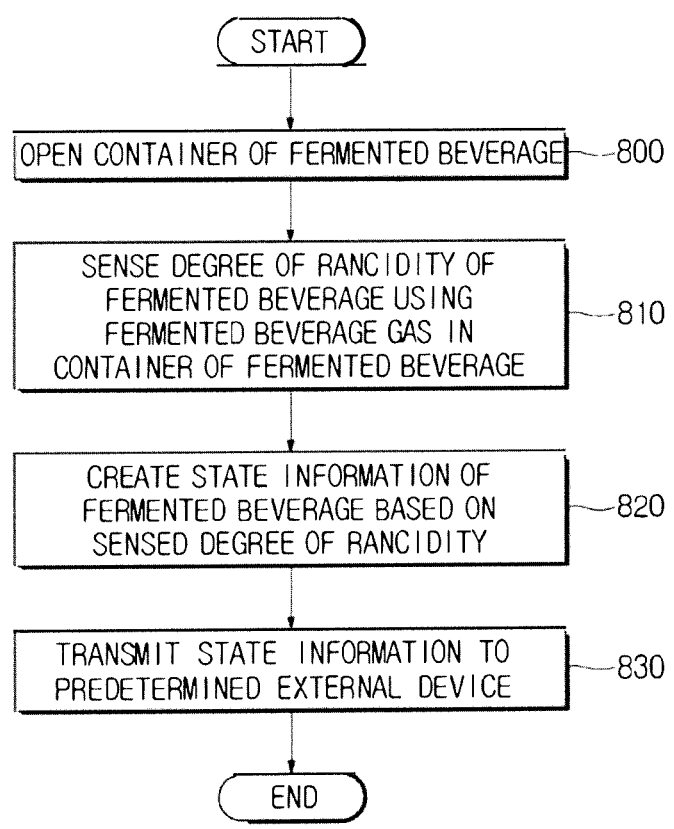
FIG. 9 is a flowchart illustrating a method of controlling a refrigerator, according to an embodiment of the present disclosure, and more specifically.

FIG. 9 is a flowchart illustrating a method of controlling a refrigerator, according to an embodiment of the present disclosure, and more specifically, FIG. 9 is a flowchart illustrating a method of transmitting state information of wine.

First, the cap opener 100 of the refrigerator may open a container of fermented beverage, in operation 800. In order to open the container of fermented beverage, a user may put the container into the inside of the cap opener 100. As a result, the opened container of fermented beverage may be positioned in the inside of the cap opener 100.

Then, the rancidity sensor 200 may sense a degree of rancidity of the fermented beverage using fermented beverage gas in the container of fermented beverage, in operation 810. In order to sense a degree of rancidity of the fermented beverage, the rancidity sensor 200 may include a polymer to absorb oxide gas produced as the results of rancidity. A change in mass of the polymer may mean an amount of oxides produced as the results of rancidity. Accordingly, the rancidity sensor 200 may sense a change in mass of the polymer, and compare the sensed change in mass of the polymer to reference data to sense a degree of rancidity of the fermented beverage.

The reference data may be decided as the results of reaction of wine with the polymer when predetermined conditions, such as the time of exposure to the air, the degree of exposure to the air, storage temperature, etc., change. The reference data may include a value of reaction of wine with the polymer at the time when rancidity occurs.

The rancidity sensor 200 may search for the sensed change in mass of the polymer in the reference data, and compare the sensed change in mass of the polymer to the value of reaction at the time when rancidity occurs, thereby sensing a degree of rancidity.

After sensing the degree of rancidity, the controller 300 may create state information of the fermented beverage based on the sensed degree of rancidity, in operation 820. Herein, the state information may be a value obtained by processing the degree of rancidity so that the user can easily recognize the degree of rancidity. The state information may include a rancidity degree percentage, a recommended drinkable period, and an expected date of rancidity, etc.

Finally, the communication unit 600 may transmit the state information of the fermented beverage to a predetermined external device, in operation 830. Herein, the predetermined external device may include all kinds of electronic devices that can transmit/receive data to/from the refrigerator according to a communication method adopted by the communication unit 600. Particularly, the predetermined external device may provide the user with the state information of the fermented beverage received from the communication unit 600, visually, acoustically, or tactually.

In this way, the refrigerator can provide information about rancidity of the fermented beverage to the user remotely.

Figure 10:
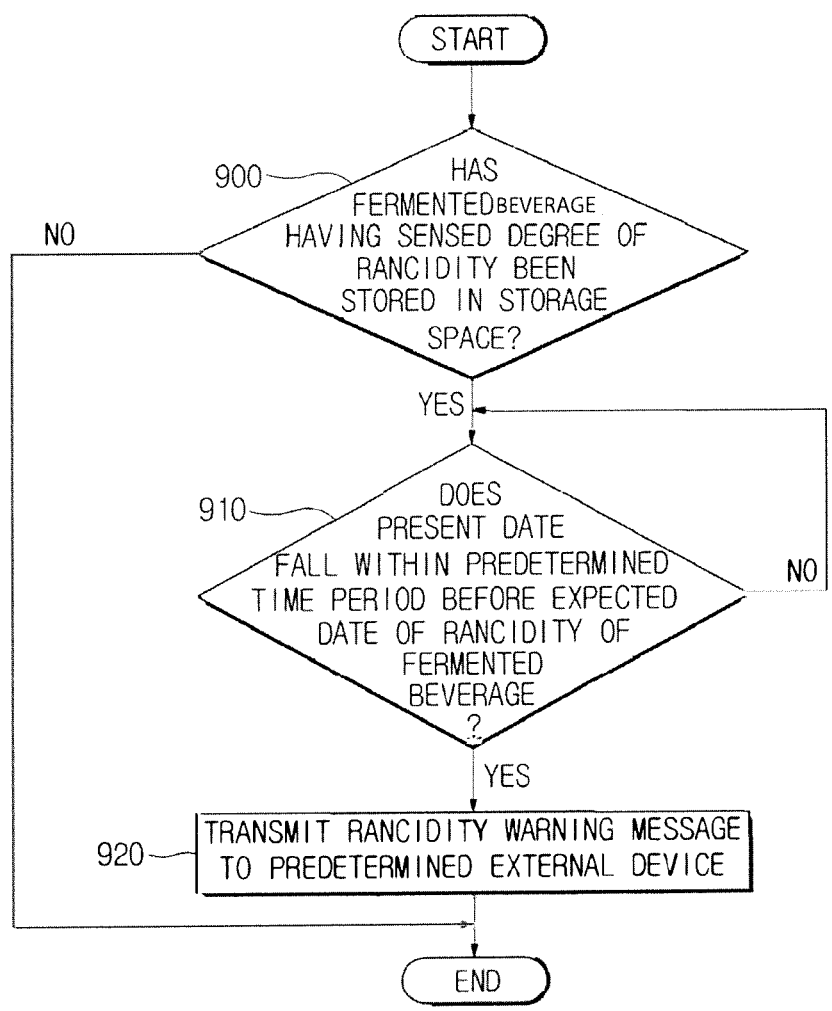
FIG. 10 is a flowchart illustrating a method of controlling a refrigerator, according to another embodiment of the present disclosure, and more particularly.

FIG. 10 is a flowchart illustrating a method of controlling a refrigerator, according to another embodiment of the present disclosure, and more particularly, FIG. 10 is a flowchart illustrating a method of transmitting a rancidity warning message, according to an embodiment of the present disclosure.

First, the controller 300 may determine whether fermented beverage having a sensed degree of rancidity has been stored in the storage space 10, in operation 900. If the controller 300 determines that no fermented beverage having the sensed degree of rancidity is found in the storage space 10, the controller 300 may terminate the process.

If the controller 300 determines that fermented beverage having a sensed degree of rancidity has been stored in the storage space 10, the controller 300 may determine whether a present date falls within a predetermined time period before an expected date of rancidity of the fermented beverage, in operation 910. The expected date of rancidity may have been decided in advance by the sensed degree of rancidity.

If the controller 300 determines that the present date does not fall within the predetermined time period before the expected date of rancidity, the controller 300 may continue to determine whether the present date falls within the predetermined time period before the expected date of rancidity.

In contrast, if the controller 300 determines that the present date falls within the predetermined time period before the expected date of rancidity, the communication unit 600 may transmit a rancidity warning message to a predetermined external device, in operation 920.

In this way, the refrigerator may inform a remote user that an expected date of rancidity is imminent, so that the user can drink the fermented beverage before the fermented beverage is rancidified.

Figure 11:
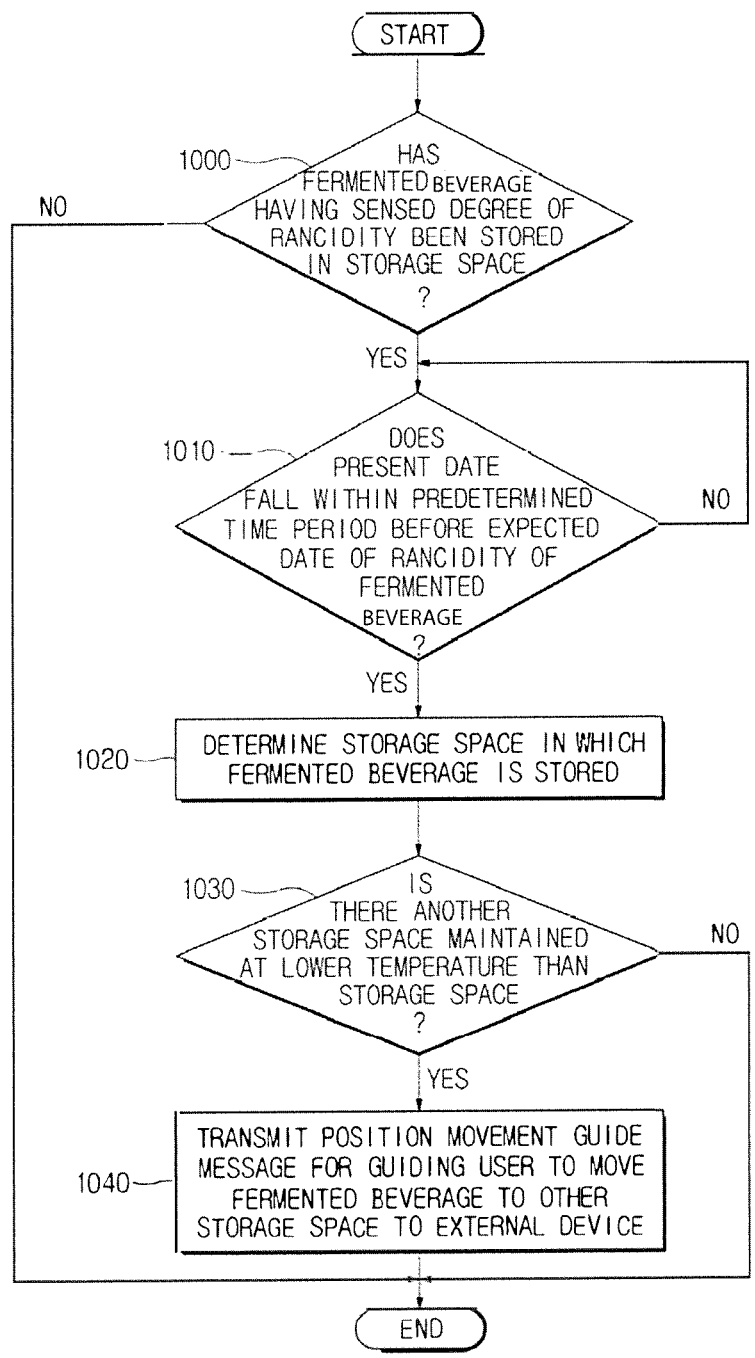
FIG. 11 is a flowchart illustrating a method of controlling a refrigerator, according to another embodiment of the present disclosure, and more particularly.

FIG. 11 is a flowchart illustrating a method of controlling a refrigerator, according to another embodiment of the present disclosure, and more particularly, FIG. 11 is a flowchart illustrating a method of transmitting a rancidity warning message, according to another embodiment of the present disclosure.

First, the controller 300 may determine whether fermented beverage having a sensed degree of rancidity has been stored in the storage space 10, in operation 1000. If the controller 300 determines that no fermented beverage having the sensed degree of rancidity is found in the storage space 10, the controller 300 may terminate the process.

If the controller 300 determines that fermented beverage having a sensed degree of rancidity has been stored in the storage space 10, the controller 300 may determine whether a present date falls within a predetermined time period before an expected date of rancidity of the fermented beverage, in operation 1010. The expected date of rancidity may have been decided in advance by the sensed degree of rancidity.

If the controller 300 determines that the present date does not fall within the predetermined time period before the expected date of rancidity, the controller 300 may continue to determine whether the present date falls within the predetermined time period before the expected date of rancidity.

However, if the controller 300 determines that the present date falls within the predetermined time period before the expected date of rancidity, the controller 300 may determine the storage space 10 in which the fermented beverage is currently stored, in operation 1020. Information about the storage space 10 in which the fermented beverage is stored may have been input in advance by a user.

After determining the storage space 10 in which the fermented beverage is stored, the controller 300 may determine whether there is another storage space that is maintained at lower temperature than the storage space 10, in operation 1030. If the controller 300 determines that there is no storage space that is maintained at lower temperature than the storage space 10, the controller 300 may terminate the process.

However, if the controller 300 determines that there is another storage space that is maintained at the lower temperature than the storage space 10, the communication unit

600 may transmit a position movement guide message for guiding a user to move the fermented beverage to the other storage space to an external device, in operation 1040.

In this way, the refrigerator may guide a remote user to move the fermented beverage to the storage space that is maintained at the lower temperature, when the expected date of rancidity is imminent, so that the user can move the fermented beverage to the storage space maintained at the lower temperature to thus delay rancidity of the fermented beverage.

Figure 12:
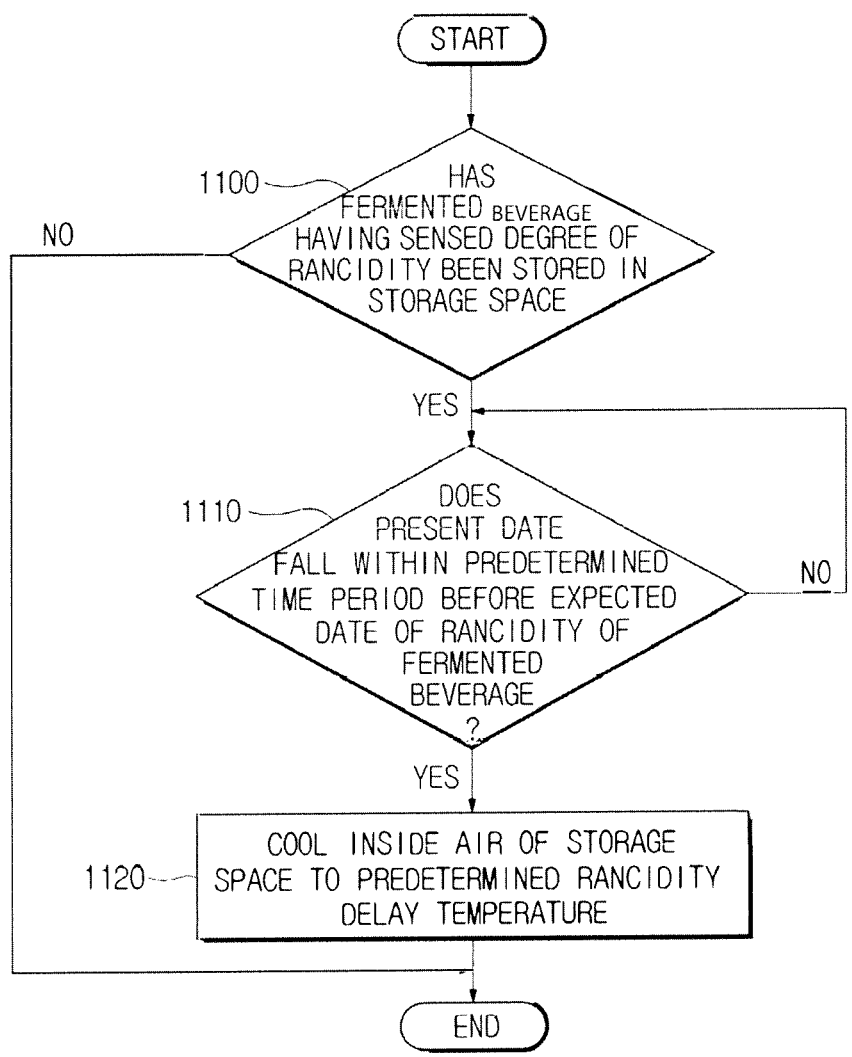
FIG. 12 is a flowchart illustrating a method of controlling a refrigerator, according to another embodiment of the present disclosure, and more particularly.

FIG. 12 is a flowchart illustrating a method of controlling a refrigerator, according to another embodiment of the present disclosure, and more particularly, FIG. 12 is a flowchart illustrating a method of cooling the inside air of a storage space to rancidity delay temperature.

First, the controller 300 may determine that fermented beverage having a sensed degree of rancidity has been stored in the storage space 10, in operation 1100. If the controller 300 determines that no fermented beverage having the sensed degree of rancidity is found in the storage space 10, the controller 200 may terminate the process.

If the controller 300 determines that fermented beverage having a sensed degree of rancidity has been stored in the storage space 10, the controller 300 may determine whether a present date falls within a predetermined time period before an expected date of rancidity of the fermented beverage, in operation 1110. The expected date of rancidity may have been decided in advance by the sensed degree of rancidity.

If the controller 300 determines that the present date does not fall within the predetermined time period before the expected date of rancidity, the controller 300 may continue to determine whether the present date falls within the predetermined time period before the expected date of rancidity.

However, if the controller 300 determines that the present date falls within the predetermined time period before the expected date of rancidity, the controller 300 may cool the inside air of the storage space 10 to predetermined rancidity delay temperature, in operation 1120. Herein, the predetermined rancidity delay temperature may mean the inside temperature of the storage space 10 for delaying the expected date of rancidity of the corresponding fermented beverage. The predetermined rancidity delay temperature may have been decided in advance based on the sensed degree of rancidity.

In this way, the refrigerator can delay rancidity of the fermented beverage without any user's manipulation.

In the refrigerator and the control method thereof according to an aspect, state information of fermented beverage can be provided to help a user drink the fermented beverage in an optimum state.

In the refrigerator and the control method thereof according to another aspect, a storing method corresponding to state information of fermented beverage can be provided to a user, or a storing method can be automatically changed to store the fermented beverage in an optimum state.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A refrigerator comprising:
   a storage space configured to store fermented beverage;
   a cooling device configured to cool air inside of the storage space;
   a rancidity sensor configured to sense a degree of rancidity of the fermented beverage;
   a communication device configured to transmit state information of the fermented beverage created based on the degree of rancidity to a predetermined external device; and
   a controller configured to create the state information of the fermented beverage based on the degree of rancidity of the fermented beverage,
   wherein the controller creates the state information of the fermented beverage, including one or more of an expected date of rancidity and a recommended drinkable period of the fermented beverage, based on the degree of rancidity of the fermented beverage.

2. The refrigerator according to claim 1, wherein the rancidity sensor senses the degree of rancidity of the fermented beverage, based on mass of the fermented beverage in a gaseous state absorbed on a plurality of different polymers.

3. The refrigerator according to claim 1, wherein when a present date falls within a predetermined time period before the expected date of rancidity or when the present date passes the recommended drinkable period, the controller controls the communication device to transmit a rancidity warning message to the predetermined external device.

4. The refrigerator according to claim 3, wherein the controller controls the communication device to transmit a rancidity warning message including a rancidity delay temperature of air inside of the storage space to the predetermined external device.

5. The refrigerator according to claim 3, wherein the storage space comprises:
   a first storage space whose inside air is cooled to a first temperature by the cooling device; and
   a second storage space whose inside air is cooled to a second temperature by the cooling device, wherein the second temperature is lower than the first temperature,
   wherein the controller controls the communication device to transmit a rancidity warning message, including a position movement guide message to guide a user to move the fermented beverage to the second storage space, to the predetermined external device.

6. The refrigerator according to claim 1, wherein when a present date falls within a predetermined time period before the expected date of rancidity or when the present date passes the recommended drinkable period, the controller controls the cooling device to cool the air inside of the storage space to a predetermined rancidity delay temperature.

7. The refrigerator according to claim 6, wherein when the controller receives a first control command to cool the air inside of the storage space to the predetermined rancidity delay temperature from the predetermined external device when the present date falls within the predetermined time period before the expected date of rancidity or when the present date passes the recommended drinkable period, the controller controls the cooling device according to the first control command.

8. The refrigerator according to claim 6, wherein when the controller receives a second control command to decide a target date of rancidity from the predetermined external device when the present date falls within the predetermined time period before the expected date of rancidity or when the present date passes the recommended drinkable period, the controller controls the cooling device to cool the air inside of the storage space to a rancidity delay temperature decided corresponding to the target date of rancidity.

9. A refrigerator comprising:
a storage space configured to store fermented beverage;
a cooling device configured to cool air inside of the storage space;
a rancidity sensor configured to sense a degree of rancidity of the fermented beverage;
a communication device configured to transmit state information of the fermented beverage created based on the degree of rancidity to a predetermined external device; and
a cap opener configured to draw a cap inserted into an opening of a container in which the fermented beverage is contained,
wherein the rancidity sensor is disposed inside of the cap opener.

10. The refrigerator according to claim 9, wherein the cap opener comprises:
a guide part configured to guide the cap inserted into the opening of the container to the inside of the cap opener; and
an uncapping part configured to draw the cap inserted inside of the cap opener along the guide part out of the opening,
wherein the rancidity sensor is disposed to face the opening of the container when the cap is drawn out of the opening.

11. The refrigerator according to claim 1, wherein the controller further creates a rancidity degree percentage as the state information of the fermented beverage, based on the degree of rancidity of the fermented beverage.

12. A method of controlling a refrigerator, the refrigerator including a storage space to store fermented beverage, the method comprising:
sensing a degree of rancidity of the fermented beverage;
creating state information of the fermented beverage based on the degree of rancidity; and
transmitting the state information of the fermented beverage to a predetermined external device,
wherein the creating of the state information of the fermented beverage comprises creating the state information of the fermented beverage, including one or more of an expected date of rancidity and a recommended drinkable period of the fermented beverage, based on the degree of rancidity of the fermented beverage.

13. The method according to claim 12, wherein the sensing of the degree of rancidity of the fermented beverage comprises sensing the degree of rancidity of the fermented beverage based on mass of the fermented beverage in a gaseous state absorbed on a plurality of different polymers.

14. The method according to claim 12, further comprising transmitting a rancidity warning message to the predetermined external device, when a present date falls within a predetermined time period before the expected date of rancidity or when the present date passes the recommended drinkable period.

15. The method according to claim 14, wherein the transmitting of the rancidity warning message to the predetermined external device comprises transmitting a rancidity warning message including a rancidity delay temperature of air inside of the storage space to the predetermined external device.

16. The method according to claim 12, further comprising cooling air inside of the storage space to a predetermined rancidity delay temperature, when a present date approaches the expected date of rancidity within a predetermined time period or when the present date passes the recommended drinkable period.

17. The method according to claim 16, wherein the cooling of the air inside of the storage space to the predetermined rancidity delay temperature comprises:
receiving a first control command to cool the air inside of the storage space to the rancidity delay temperature from the predetermined external device, when a present date falls within a predetermined time period before the expected date of rancidity or when the present date passes the recommended drinkable period; and
cooling the air inside of the storage space according to the first control command.

18. The method according to claim 16, wherein the cooling of the air inside of the storage space to the predetermined rancidity delay temperature comprises:
receiving a second control command to decide a target date of rancidity from the predetermined external device, when the present date falls within the predetermined time period before the expected date of rancidity or when the present date passes the recommended drinkable period; and
cooling the air inside of the storage space to a rancidity delay temperature decided corresponding to the target date of rancidity.

19. The method according to claim 12, further comprising, when a present date falls within a predetermined time period before the expected date of rancidity or when the present date passes the recommended drinkable period, transmitting, to the predetermined external device, a position movement guide message to guide a user to move the fermented beverage stored in a first storage space whose inside air is maintained at a first temperature to a second storage space whose inside air is maintained at a second temperature that is lower than the first temperature,
wherein the first storage space and the second storage space are provided in the storage space.

20. The refrigerator according to claim 12, wherein the creating of the state information of the fermented beverage further comprises creating a rancidity degree percentage as the state information of the fermented beverage, based on the degree of rancidity of the fermented beverage.

* * * * *